United States Patent [19]

Brown

[11] 4,359,334

[45] Nov. 16, 1982

[54] COMPOSITION FOR PLANT GROWTH REGULATION

[75] Inventor: Michael J. Brown, Randolph, N.J.

[73] Assignee: GAF Corporation, New York, N.Y.

[21] Appl. No.: 144,504

[22] Filed: Apr. 28, 1980

[51] Int. Cl.³ .............................................. A01N 43/36
[52] U.S. Cl. ............................................ 71/95; 71/74; 71/94; 71/103
[58] Field of Search ............................... 71/103, 95, 94

[56] References Cited

U.S. PATENT DOCUMENTS

| 3,885,951 | 5/1975 | Hofer et al. | 71/103 |
| 4,191,555 | 4/1980 | Kliegman | 71/95 |

FOREIGN PATENT DOCUMENTS 657536 2/1966 Belgium .
6905393 4/1971 South Africa .
369889 2/1973 U.S.S.R. .

OTHER PUBLICATIONS

Collective Index, vol. 76-85, (1972-1976), Chem. Abst., p. 34553.

Primary Examiner—Catherine L. Mills
Attorney, Agent, or Firm—James Magee, Jr.; Marilyn J. Maue

[57] ABSTRACT

This invention relates to a composition comprising a mixture of a N-heterocyclic amide, such as N-methylpyrrolidone, and a 2-haloethylsulfinate having from 3 to 22 carbon atoms for the treatment of plants, including trees, shrubs, farm crops and ornamentals to achieve promotional and sustained hormonal ethylene plant growth regulatory effects; and the method of using and preparing said composition.

15 Claims, No Drawings

COMPOSITION FOR PLANT GROWTH REGULATION

The present invention is particularly directed to the promotion and extension of high activity in the plant growth response to haloethylsulfinates disclosed in U.S. Pat. No. 3,885,951, issued May 27, 1975; the entire teaching therein with respect to 2-haloethylsulfinate compounds being incorporated herein by reference. Accordingly, it is an object of the present invention to provide an interacting multicomponent composition for sustaining and increasing plant response to said sulfinate compounds, particularly beneficial in the treatment of seeds to promote germination and development through the seedling stage to harvestability for various plant species such as cotton, bananas, soybeans and other crops responsive to hormonal ethylene effects to advance crop maturation while slowing defoliation, retarding senescence in grasses, developing shorter bushier plants having increased fruit set sites and significantly increasing ethylene generation.

Another object is to provide the above advantages while simultaneously reducing plant susceptibility to lodging.

Still another object is to provide an ecologically safe composition for the treatment of plants and an economical method for its application.

These and many additional objects and advantages will become apparent from the following description and disclosure.

According to this invention, there is provided an interacting mixture for preharvest or postharvest treatment of a plant, plant part or plant situs which comprises as active ingredients, a N-heterocyclic amide, such as for example N-methylpyrrolidone or polyvinylpyrrolidone, and a sulfinate capable of generating ethylene, having the formula:

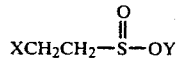

wherein X is a fluorine, chlorine, bromine or iodine atom and Y is alkyl or alkenyl of 1 to 20 carbon atoms optionally substituted with halogen including linear, cyclic and branched chain groups.

Examples of suitable N-heterocyclic amides include N-methyl-2-pyrrolidone, 2-pyrrolidone, polyvinylpyrrolidone having from 2 to 5,000 monomer units, N-methyl-2-pyridone, N-methyl-2-piperidone, N-methyl-2,5-succinimide, succinimide, N-(o-tolyl)-2-pyrrolidone, N-(2-hydroxyethyl)-2-pyrrolidone, and isomers and mixtures of these amides with other heterocyclic amides or with linear amides such as the methyl substituted acetamide or formamide, eg. dimethyl acetamide, methyl acetamide and methyl formamide or amines. Of these amide components, the tertiary amides having one hetero-nitrogen atom per 5- or 6-membered heterocyclic ring are preferred and N-methylpyrrolidone is most preferred.

It has now been discovered that a N-heterocyclic compound of this invention, having from 4 to 5 carbon atoms in a 5- or 6-membered ring, when combined with the above described sulfinates significantly increases the amount of ethylene generation and metabolic growth promotional activity over a longer duration than would be obtained with sulfinate per se. This result is wholly, unexpected since, except for moderate defoliation, the N-heterocyclic compounds have been regarded as inert solvents or dispersants for water-insoluble compounds and have been shown to have no metabolic plant growth regulating properties when employed in mixtures. Accordingly, it would be expected that the addition of such heterocyclics to a highly active plant growth promoter would have no promotional effect on ethylene generation or any sustaining influence on growth regulation. Instead it is found that the promotional effects of the sulfinate compound are significantly extended and increased.

The sulfinates of the present invention include the methyl, ethyl, propyl, isopropyl, butyl, isobutyl, pentyl, isopentyl, hexyl, isohexyl, cyclohexyl, 1,2-dimethylbutyl, 4,4-dimethylbutyl, heptyl, octyl, 2,4,6,7-tetramethyl-octyl, nonyl, decyl, dodecyl, hexadecyl, octadecyl, 2,4-dimethyloctadecyl, chloroethyl, bromoethyl, 2,3-dibromobutyl, 1,3-dichlorobutyl, octenyl, decenyl, dodecenyl, allyl, hexenyl, butenyl, 4-chlorobutenyl-2, 2,4,6-trichlorooctenyl-4, etc. esters of a 2-haloethyl sulfinic acid. Of these, the saturated hydrocarbon alkyl esters having from 1 to 10 carbon atoms are preferred and, of these esters, 2-chloroethyl- or 2-bromoethyl-sulfinic acid esters are most preferred.

The following discussion is directed to the preferred mixture, involving N-methyl-2-pyrrolidone and a 2-haloethylsulfinate, however it is to be understood that any of the other N-heterocyclic compounds described above or their mixtures with other N-heterocyclic amides or with linear methyl substituted amides such as dimethylacetamide, methyl formamide, methylacetamide can be substituted in the following discussion or in the examples to provide the benefits described.

The proportion of N-methylpyrrolidone to 2-haloethylsulfinate employed in the present invention can vary between about 0.05:1 and about 5:1, preferably between about 0.5:1 and about 3:1. For economy and for more uniform coverage, the mixture or the individual components thereof are incorporated in a conventional inert carrier or diluent which is conveniently a liquid selected from the group comprising water, a methyl substituted benzene, cyclohexane and other higher boiling paraffins, vegetable or mineral oil or oil fraction such as a petroleum oil fraction, a fatty alcohol or ketone or any compatable mixture of the above. Of these, water is the most desirable because of its availability; although when the sulfinate portion of the mixture is in high excess, a surfactant or emulsifier is advantageously added to the composition. Such adjuvants, when employed, comprise between about 0.001% and about 20% of the sulfinate component. Although any of the usual inert emulsifiers or surfactants can be employed, particularly recommended are the nonionics and anionics such as polyethylene- or polypropylene- glycols, polyoxyethylene- or polyoxypropylene- glycols, polyoxyethylene- or polyoxypropylene- ethers, alkyl or aryl sulfates or sulfonates, lignin, methyl cellulose, etc. The present compositions contain from about 0.05% to about 70%, preferably from about 1% to about 60% by weight of the active mixture. As a liquid formulation, the mixture with liquid carrier can be employed as a solution, an emulsion or dispersion. The formulation can also contain other adjuvants such as a thickening agent, eg. any of the conventionally employed gums or resins including locust bean gum, low molecular weight polymers, etc. for application in areas of high rainfall.

It is to be understood, however, that the present mixture can also be applied to a plant, plant part or plant situs as a paste, as a powder or as a course granulated solid by the use of such dry extenders as talc, bentonite clay, sand, diatomaceous earth, kaolin, petrolatum pastes or jellies or other standard extenders. The concentration of the mixture in these extenders is substantially the same as recited above for liquid carriers.

In general, the concentration of N-methylpyrrolidone or amide with respect to the plant or plant part can vary within a wide range between about 10 ppm and about 20,000 ppm, preferably between about 75 ppm and about 5,000 ppm, depending on the effect desired, the plant treated, the climatic conditions at the time of application and the maturity of the plant.

The formulations or compositions of the present invention can be prepared by any one of several convenient methods. For example, the sulfinate and the N-heterocyclic amide can each be separately dissolved in, or admixed with, the same or different solvents or carriers and then combined before applying to the plant, plant part or plant situs or the components in the same or individual carriers can be combined upon application to the plant. Alternatively, both components can be simultaneously or sequentially dissolved in, or admixed with the same carrier to provide the desired composition. Adjuvants can be added to either component-carrier composition, before or after combination of the components. In certain instances it may be desireable to form a composition with a liquid carrier for one of the components, eg. an aqueous solution of N-methylpyrrolidone, and a second composition with a dry carrier for the remaining component, after which the components may be mixed to form a paste or viscous liquid which is resistant to removal by rain or such subsequent treating operations as the consumer may require, eg. separate application of a fungicidal, a selective herbicidal, pesticidal or defoliant spray.

The present formulations may also contain additional plant growth regulating compounds or compositions and other agricultural chemicals such as a fungicide, herbicide, nematocide or pesticide or combinations of these, provided that the additives do not materially alter the activity of the present mixture.

The above compositions or formulations are applied to a plant, a plant part or the situs from which seedlings will emerge by spraying, dusting, atomizing, broadcasting, immersing or washing as convenient for the particular operation. Generally, plant dosage levels between about 0.0005 and about 0.5 gram, more desirably between about 0.003 and about 0.1 gram, per plant of N-methylpyrrolidone in the above mixture is applied to obtain the increased and sustained activity of the sulfinate compound. The plant is contacted with the present mixture at a rate of from about 0.1 to about 100 kg per hectare, more usually from about 1 to about 10 kg per hectare of soil area.

By way of illustration, in the preharvest treatment of cotton the present mixture of components is applied prior to harvest and after boll set, for example application of from about 200 ppm to about 5,000 ppm of mixture in a carrier is preferably effected at least 30 days after square set; although it is to be understood that application can be made at any time after square set up through initial boll break without causing any damage to the plant or plant fiber.

The advantages realized from application of the present composition in the preharvest treatment of cotton are enumerated as follows.

1. Providing a composition for effecting rapid boll ripening, boll dehiscence and leaf defoliation so as to avoid the need for multiple chemical applications.
2. Increasing the rate of immature boll dehiscence so as to provide more uniformly opened bolls for first harvest collection and synchronizing defoliation so that it is effected when the bolls are fully developed and opening or opened.
3. Providing coaction between the active ingredients of the composition to produce metabolic ethylene effects in increasing dehiscence.
4. Advancing early dehiscence of bolls containing mature fibers while having substantially no effect on the completely matured breaking bolls so as to increase the proportion of recoverable cotton in a single, first harvest and to minimize and/or obviate the necessity of a second harvest.
5. Providing cotton fiber of inherent high quality.
6. Reducing plant temperature sensitivity and resistance to low temperature dehiscence.
7. Permitting later planting of crop and/or earlier harvesting.
8. Providing economic and labor saving harvest of cotton.

In the case of soybeans and cereal grasses, the present mixtures promote shorter sturdier stems and offer extended protection against lodging. These mixtures also prevent excessively rapid defoliation so as to conserve transpiration as the underdeveloped crop matures to harvestability. To obtain these beneficial effects, between 1,000–3,000 ppm of a 1:2 to 2:1 molar mixture of N-methyl pyrrolidone/sulfinate was sprayed to drench on seedlings. Omission of N-methylpyrrolidone in the composition results in rapid defoliation before 80% of the crop has reached maturity and taller, thinner plant stems were produced which resulted in a significant increase in lodging.

As an example of ripening of picked fruit, 500–600 ppm sulfinate and 300–400 ppm N-methylpyrrolidone dissolved in about 10% aqueous acetone solution is suitably employed to ripen green picked bananas 6–8 days sooner than untreated fruit from the same stalk after being immersed in the solution for 0.5–1.5 hours. Omission of the N-methylpyrrolidone in the above composition led to fruit yellowing 2–4 days after those ripened with the present mixture.

When used alone, the N-heterocyclic compounds of the present invention behave as ethylene inhibitors as shown by the following examples 1–19. Accordingly, it is all the more surprising that they induce a promotional ethylene generating effect when combined with the present sulfinates. In accordance with the following Examples 1–19, the ethylene inhibiting effect of various N-heterocyclic amides is measured and reported in Table I.

EXAMPLES 1–19

In a growth chamber maintained at 30° C. and 2,000–3,000 foot candle light, soybean plants from the same seed source were grown to various stages of development. Each of the following experiments were carried out in quadruplicate, and the results (found to be highly reproducible), were averaged and reported in Table I below.

In the following Examples 1-19, leaf disc samples from (a) plant seedlings about 2 weeks old (Examples 1-4); (b) underdeveloped plants at the trifoliate stage (Examples 5-8); (c) fully developed plants with no further growth increase (Examples 9-12); (d) a second group of fully developed plants (Examples 13-16); and (e) a third group of fully developed plants (Examples 17-19), were removed by cutting the leaf with a circular cork borer. Each leaf disc sample was immersed for 30 minutes in a 100 milliter aqueous solution containing water as a control or aqueous solutions containing 1,000 ppm and 3,000 ppm of the compound to be tested. At the end of 30 minutes the leaf disc was removed from its solution, patted dry and inserted into a 25 ml glass vial equipped with a septum through which a syringe could be inserted for extracting a sample of the supernatant air above the leaf disc. Examples 1 through 16 were allowed to stand in the light for one hour and Examples 17 through 19 were allowed to stand in the light for 16 hours, after which a gas sample above the leaf in the vial was removed and analyzed for ethylene by gas liquid phase partition chromatography. Comparison with the control, reported in nanoliters of ethylene per liter of air per 10 cm$^2$ of leaf surface, are presented in the following Table (based on an average of 4 replicate samples). For the purpose of comparison, the control was assigned a value of 1.0 and the test compounds were reported as the percent deviation from the control.

Each of the foregoing experiments was repeated, except that the leaf disc samples were similarly treated and held in the dark for the above periods prior to analysis of the gas samples. The results of these experiments are also reported in Table I.

TABLE I

| Ex. No. | TEST COMPOUND | C$_2$H$_4$ GENERATED BASED ON CONTROL | | | |
|---|---|---|---|---|---|
| | | 1000 ppm | | 3000 ppm | |
| | | Light | Dark | Light | Dark |
| 1. | Control (water) = 500 nl C$_2$H$_4$/1/10cm$^2$ | 1.0 | 1.0 | 1.0 | 1.0 |
| 2. | N-(hydroxyethyl)-2-pyrrolidone | −38% | −25% | −45% | −32% |
| 3. | 2-Pyrrolidone | −73% | −69% | −78% | −75% |
| 4. | N-methyl-2-pyrrolidone | −84% | −82% | −91% | −91% |
| 5. | Control (water) = 640 nl C$_2$H$_4$/1/10cm$^2$/10 cm$^2$ | 1.0 | 1.0 | 1.0 | 1.0 |
| 6. | N-methyl-2-piperidone | −38% | −60% | +150% | +110% |
| 7. | N-methyl-2-pyridone | −50% | −55% | +130% | +115% |
| 8. | N-methyl-2-pyrrolidone | −50% | −65% | −65% | −90% |
| 9. | Control (water) 640 nl C$_2$H$_4$/1/10cm$^2$ | 1.0 | 1.0 | 1.0 | 1.0 |
| 10. | N-(hydroxyethyl)-2-pyrrolidone | −15% | +120% | +185% | +250% |
| 11. | 2-pyrrolidone | −40% | −24% | +120% | +166% |
| 12. | N-methyl-2-pyrrolidone | −50% | −50% | −61% | −60% |
| 13. | Control (water) = 640 nl C$_2$H$_4$/1/10cm$^2$ evolved/10 cm$^2$ | 1.0 | 1.0 | 1.0 | 1.0 |
| 14. | N-methyl-2-pyrrolidone | −50% | −60% | −20% | −40% |
| 15. | N-(methyl)-2-piperidone | +40% | −50% | +190% | — |
| 16. | N-methyl-2-pyridone | −80% | −50% | −40% | +170% |
| 17. | Control (water) = 500 nl C$_2$H$_4$/1/10cm$^2$ evolved/10 cm$^2$ | 1.0 | — | 1.0 | — |
| 18. | 2-pyrrolidone | −40% | — | °104% | — |
| 19. | N-methyl-2-pyrrolidone | −50% | — | −46% | — |

It is noted that certain of the heterocyclic agents in the above table provide an ethylene generating effect at the higher 3,000 ppm concentration and that this effect occurs in older plant tissue which has less tolerance for excessive amounts of certain N-heterocyclic agents and therefore an increase marked by the generation of ethylene is observed as the response to a stress effect induced by the chemical. In these cases, it is also noted that the agent generally reaches an efficacy threshold at a concentration less than 3,000 ppm, e.g. 1,000-2,000 ppm. Specifically, at about 2,000 ppm, a maximum response is obtained and amounts in excess of about 2,000 ppm are unable to provide additional inhibition of ethylene; in fact, concentrations of 3,000 ppm often induce a stress situation where the opposite result, namely increased ethylene generation, is observed. Accordingly, with the exception of 2-pyrrolidone, N-methyl pyrrolidone and polyvinylpyrrolidone, the selection of the amide component in the present mixture is partly dependent on the age of the plant.

The addition of equimolar amounts of any of the above heterocyclic amides or polyvinylpyrrolidone significantly increases the initial young plant response to 2-chloroethylsulfinate, or other sulfinates of this invention, in solution, eg. a 10% aqueous alcoholic solution containing 1,000 ppm ester, by at least 20% and higher depending on the amide employed. On fully matured plant tissue the enhancing effect for these amides is at least 5%.

Sustained activity of the sulfinate plant growth regulant is observed in the dehiscence of cotton bolls and ripening of fruit, which responses are typical hormonal effects of ethylene generation. Specifically, a group of untreated 12-week old hirsuiti cotton plants exhibit a 75% normal boll opening at 45 to 60 days after square set. For example, spraying of hirsuiti cotton crop 15 days after square set with, 1,000 ppm butyl-2-chloroethyl sulfinate solution, results in 75% boll opening 10 days after spraying, and 85%, by the 12th day, after spraying. Upon addition of 800 ppm N-methyl-2-pyrrolidone to the sulfinate solution, 85% of the bolls are opened on the 10th day after spraying and, by the 12th day, the number of opened bolls is increased to 95-100%.

It is also noted that cotton, tomato and pea plants sprayed with the present mixtures have a shorter more branching structure offering more crop sites than the corresponding untreated or sulfinate acid treated plants.

Promotion of seed germination with the present mixtures is effected at lower dosage levels, eg. 25 to 500 ppm of mixture wherein amide:ester mole ratio is between about 0.05:1 and about 4:1. By way of example 100 ppm aqueous solutions of ethephon, 2-bromoethylsulfinic butyrate and 2-bromoethylsulfinic butyrate/2-pyrrolidone in a 1:0.4 mole ratio are compared for promotion of wheat seed germination after treating 3 separate humidity and temperature controlled plots containing 100 seeds each with 0.5 liter of each solution. An additional plot is reserved as a control. After 10 days, the control plot provided only 25% germination, the ethephon treated plot produced 55% germination; the sulfinic ester treated plot achieved about 85% germination and the plot treated with the present mixture provided 87% germination.

EXAMPLES 20 THROUGH 24

Comparison of Plant Growth Regulants on In Vivo Production of Ethylene in Soybean Leaf Tissue Twenty-eight leaf discs, cut with a 1.76 cork borer from soybean plants grown to the unifoliate leaf stage in a greenhouse maintained at 26°–30° C., on a 16 hour photoperiod, were floated on 25 ml of aqueous solution in a closed Petri dish. Two solutions (i.e., 1000 ppm and 3000 ppm) were prepared for each compound to be tested and 4 discs were floated in each solution, including one water solution to serve as control. After floating on the solutions for 30 minutes the discs were removed, blotted dry with paper towelling, and the four discs from each solution were placed in a separate 8 ml vial fitted with a septum through which the internal atmosphere of each vial could be sampled by insertion of a 1 ml syringe. Four replicate vials were thus prepared for each treatment. The vials were allowed to stand in light for 1 hour, after which the gas sample was withdrawn and analyzed by gas-liquid chromatography. The vials were then stored in the dark for 16 hours after which additional gas samples were withdrawn and analyzed. Results of the analyses are reported as nannoliters of ethylene per liter of atmosphere per $cm^2$ of leaf sample per mmole of test compound in following Table 2.

TABLE 2

| | | nl ethylene/l/$cm^2$/mmole | | | |
|---|---|---|---|---|---|
| | | 1 hour | | 16 hours | |
| Ex. No. | Compound | 1000 ppm | 3000 ppm | 1000 ppm | 3000 ppm |
| 20 | (a)$ClC_2H_4S\overset{O}{\underset{\|}{—}}OC_4H_9$ | 19,536 | 9,820 | 82,144 | 27,243 |
| 21 | (b)$ClC_2H_4P\overset{O}{\underset{\|}{\diagup}}\diagdown\underset{OH}{OH}$ | 3,102 | 660 | 32,307 | 23,167 |
| 22 | 1:1 molar mixture NMP/(a) | 15,340 | 17,885 | 101,450 | 79,763 |
| 23 | 1:1 molar mixture 2-pyrrolidone/(a) | 15,900 | 16,850 | 90,500 | 50,600 |
| 24 | 1:1 molar mixture PVP/(a) | 10,100 | 12,500 | 45,000 | 49,000 |

Untreated leaf discs yielded 42.6 nl/l after 1 hour and 114.7 nl/l after 16 hours.
NMP = N—methyl-2-pyrrolidone
PVP = polyvinylpyrrolidone K30

When the above solutions of examples 22, 23 and 24 are individually sprayed on 3 groups of 10 soybean plants growing in a greenhouse, the fruit ripened in all 3 cases at least 10 days before untreated control plants and the rate of ripening is found to be directly proportional to the amount of ethylene generated.

EXAMPLE 25

Enhancement of Fruit Harvest

Twenty navel orange trees sprayed to drench three days before harvest, with an aqueous solution containing 2,500 ppm, of a 1:2 molar mixture of N-methyl-2-pyrrolidone and methyl-2-chloroethylsulfinate, show significant reduction in pull force 3 days after spraying, (6 pounds) as compared with twenty untreated trees growing under the same conditions and at the same stage of development requiring 15 pounds pull force. The present mixture is also a fruit harvest aid for other fruit trees such as, for example, cherry, apple, peach, pear, lemon, lime, apricot, grapefruit, plums and olive trees.

Higher concentrations of the above mixture e.g. 5,000 ppm is useful for thinning fruit trees after fruit set.

EXAMPLE 26 THROUGH 40

Fruit Ripening Activity

Fifteen groups of 3 green bananas of uniform size and stage of development are picked from 3 stalks grown under the same conditions and separately sprayed with 20 ml of an aqueous plant growth promoting solution containing 10% methanol, 2% polyethylene sorbitan monolaurate and 1000 ppm of a plant stimulating agent designated in Table 3.

Doubling the concentration of the stimulating agent and repeating the above procedure, in many cases, provides better results.

The acceleration of ripening in days is determined by comparison with 3 untreated bananas as a control. The active promotor and its concentration together with the days in which the treated fruit ripened before the untreated control fruit at both concentration levels is shown in the following Table 3.

TABLE 3

| | | Acceleration of Ripening Days Before Control | |
|---|---|---|---|
| Ex. No. | Active Promoter Agent | 1000 ppm | 2000 ppm |
| 26. | Ethephon** | 10 | 10 |
| 27. | isopropyl-2-chloroethylsulfinate | 11 | 11 |
| 28. | butyl-2-chloroethylsulfinate | 11 | 11 |
| 29. | vinyl-2-chloroethylsulfinate | 13 | 13 |
| 30. | 2-ethylhexyl-2-chloroethylsulfinate | 12 | 12 |
| 31. | allyl-2-chloroethylsulfinate | 12 | 13 |
| 32. | eicosyl-2-chloroethylsulfinate | 13 | 13 |
| 33. | compd. of Ex. 27 + NMP* (1:1 molar) | 12 | 15 |
| 34. | compd. of Ex. 28 + NMP (1:1 molar) | 12 | 13 |
| 35. | compd. of Ex. 29 + NMP (1:1 molar) | 15 | 16 |
| 36. | compd. of Ex. 30 + NMP (1:1 molar) | 13 | 14 |
| 37. | compd. of Ex. 31 + NMP (1:1 molar) | 14 | 15 |
| 38. | compd. of Ex. 32 + NMP (1:1 molar) | 14 | 14 |
| 39. | compd. of Ex. 28 + 2-pyrrolidone (1:1 molar) | 12 | 13 |
| 40. | compd. of Ex. 31 + 2-pyrrolidone (1:1 molar) | 12 | 12 |

*NMP is N—methyl-2-pyrrolidone
**Ethephon is 2-chloroethylphosphonic acid

It is to be understood that any of the corresponding bromo analogs of the above 2-chloroethylsulfinates can be substituted in examples 33–40 to provide similar results. Also any of the other N-heterocyclic amides described herein, e.g. maleic hydrazide, N-methyl-2-pyridone polyvinylpyrrolidone K30-K90, etc. can be substituted in examples 33–40 to provide increased fruit ripening.

EXAMPLES 41 THROUGH 55

Promotion of Seed Germination

Fourteen groups of 20 sunflower seeds from the same seed source at the same stage of development are separately immersed for 1.5 hours in separate aqueous 10% methanol solutions each containing 5% polyoxyethylene glycol surfactant and 150 ppm of a different plant growth regulating agent as defined in Table 4. An additional solution containing no plant growth regulating agent is provided as a control in which 20 additional seeds are immersed for the same period. The number of seeds germinated for each treatment 5 days after immersion when planted in flats and exposed to standard light and humidity conditions in a greenhouse, is shown below.

TABLE 4

| | Active Regulant | Seed Germination % |
|---|---|---|
| 41. | Ethephon | 10 |
| 42. | Ethyl-2-chloroethysulfinate | 16 |
| 43. | Isopropyl-2-choroethylsulfinate | 16 |
| 44. | Butyl-2-chloroethylsulfinate | 13 |
| 45. | Cyclohexy-2-chloroethylsulfinate | 15 |
| 46. | 2-chloroethyl-2-chloroethylsulfinate | 17 |
| 47. | 8-chlorooctyl-2-bromoethylsulfinate | 11 |
| 48. | None | 4 |
| 49. | Compound of 42 + NMP (1:1 molar mix) | 18 |
| 50. | Compound of 43 + NMP (1:1 molar mix) | 18 |
| 51. | Compound of 44 + NMP (1:1 molar mix) | 16 |
| 52. | Compound of 45 + NMP (1:1 molar mix) | 17 |
| 53. | Compound of 46 + NMP (1:1 molar mix) | 19 |
| 54. | Compound of 47 + NMP (1:1 molar mix) | 12 |
| 55. | Compound of 44 + PVP K30 (6:1 molar mix) | 19 |

It is to be understood that any of the agents of Examples 49–55 can be substituted in examples 22–25 and 33–40, and any of the N-heterocyclic amides described herein or any combination of these can be substituted in examples 33–40, and 49–55 to provide the improvements described.

The above represent preferred examples involving the use of the present compositions. However, it is to be understood that any of the other N-heterocyclic amides defined in the foregoing disclosure, particularly 2-pyrrolidone, N-methyl pyrrole, maleic hydrazide and polyvinyl-pyrrolidone K30 to K90, as well as any of the other alkyl, alkenyl or heterocyclic esters or other haloethyl sulfinates described herein can be substituted in the above examples 22–25, 33–40 and 49–55 to provide the benefits described therein.

It should also be recognized that the molar proportion of ester to amide in these mixtures can be lowered to 0.2:1 when a somewhat slower ripening or hormonal ethylene effect is desired or the proportion of ester can be raised to 20:1 ester to amide without materially affecting the rate of plant response.

What is claimed is:

1. A coacting plant growth promoting composition consisting essentially of a 2-haloethyl sulfinate having the formula:

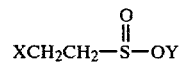

wherein X is a halogen atom and Y is alkyl or alkenyl of 1 to 20 carbon atoms optionally substituted with halogen and a promotional ethylene generating amount of a pyrrolidone selected from the group consisting of N-methylpyrrolidone, pyrrolidone, and polyvinylpyrrolidone in a mole ratio of between about 0.5:1 and about 3:1.

2. The composition of claim 1 wherein said sulfinate is a 2-chloroethylsulfinate.

3. The composition of claim 2 wherein said sulfinate is methyl-2-chloroethylsulfinate.

4. The composition of claim 2 wherein said sulfinate is isopropyl-2-chloroethylsulfinate.

5. The composition of claim 2 wherein said sulfinate is butyl-2-chloroethylsulfinate.

6. The composition of claim 1 wherein said sulfinate is a 2-bromoethylsulfinate.

7. The composition of claim 6 wherein said sulfinate is methyl-2-bromoethylsulfinate.

8. The composition of claim 7 wherein said sulfinate is ethyl-2-bromoethylsulfinate.

9. The composition of claim 7 wherein said sulfinate is allyl-2-bromoethylsulfinate.

10. The process of producing enhanced hormonal ethylene plant response by contacting the plant with a coacting mixture of claim 1.

11. The process of claim 10 wherein the concentration of the coacting mixture in a carrier to form a composition is between about 50 ppm and about 25,000 ppm.

12. The process of claim 11 wherein the composition is applied to the plant as a liquid spray.

13. The process of claim 10 wherein the plant is contacted with an aqueous solution of said mixture.

14. The process of claim 11 wherein the composition additionally contains a surfactant.

15. The process of claim 11 wherein the composition additionally contains a thickener.

* * * * *